(12) United States Patent
Russell et al.

(10) Patent No.: US 10,100,178 B2
(45) Date of Patent: Oct. 16, 2018

(54) BIOPOLYMER BLENDS AS EMULSION STABILIZERS

(71) Applicant: Akzo Nobel Chemicals International B.V., Arnhem (NL)

(72) Inventors: Michael J. Russell, Madison, NJ (US); Qiwei He, Belle Mead, NJ (US); John Socrates Thomaides, Berkeley Heights, NJ (US); Gary Theodore Martino, Monmouth Junction, NJ (US); Gloria Cansanay Tirol, Kendall Park, NJ (US)

(73) Assignee: AKZO NOBEL CHEMICALS INTERNATIONAL, B.V., Arnhem (NL)

( * ) Notice: Subject to any disclaimer, the term of this patent is extended or adjusted under 35 U.S.C. 154(b) by 0 days.

(21) Appl. No.: 15/560,254

(22) PCT Filed: Mar. 29, 2016

(86) PCT No.: PCT/EP2016/056763
§ 371 (c)(1),
(2) Date: Sep. 21, 2017

(87) PCT Pub. No.: WO2016/156289
PCT Pub. Date: Oct. 6, 2016

(65) Prior Publication Data
US 2018/0066127 A1    Mar. 8, 2018

Related U.S. Application Data

(60) Provisional application No. 62/141,442, filed on Apr. 1, 2015.

(30) Foreign Application Priority Data

Apr. 21, 2015    (EP) .................................. 15164393

(51) Int. Cl.
| | | |
|---|---|---|
| *A61K 8/00* | (2006.01) | |
| *C08L 1/28* | (2006.01) | |
| *C08L 3/08* | (2006.01) | |
| *A61Q 5/06* | (2006.01) | |
| *A61K 8/73* | (2006.01) | |
| *A61K 8/06* | (2006.01) | |

(52) U.S. Cl.
CPC .............. *C08L 1/284* (2013.01); *A61K 8/062* (2013.01); *A61K 8/731* (2013.01); *A61K 8/732* (2013.01); *A61Q 5/06* (2013.01); *C08L 3/08* (2013.01)

(58) Field of Classification Search
None
See application file for complete search history.

(56) References Cited

U.S. PATENT DOCUMENTS

| | | | |
|---|---|---|---|
| 4,228,277 A | 10/1980 | Landoll | |
| 5,104,646 A | 4/1992 | Bolich, Jr. et al. | |
| 6,528,575 B1 | 3/2003 | Schade et al. | |
| 2002/0012645 A1* | 1/2002 | Midha ................... | A61K 8/025 424/70.2 |
| 2004/0234486 A1 | 11/2004 | Hashimoto | |
| 2005/0107503 A1 | 5/2005 | Couillet et al. | |
| 2008/0190615 A1 | 8/2008 | Drochon | |
| 2009/0111716 A1 | 4/2009 | Hough et al. | |
| 2011/0198089 A1 | 8/2011 | Panga et al. | |
| 2012/0024529 A1 | 2/2012 | van Zanten et al. | |
| 2012/0121519 A1 | 5/2012 | Thomaides et al. | |
| 2014/0262293 A1 | 9/2014 | Song et al. | |

FOREIGN PATENT DOCUMENTS

| | | |
|---|---|---|
| WO | 2006/130675 A2 | 12/2006 |
| WO | 2007/038745 A1 | 4/2007 |
| WO | 2007/141731 A1 | 12/2007 |
| WO | 2009/080657 A1 | 7/2009 |
| WO | 2009/080659 A2 | 7/2009 |
| WO | 2011/100665 A2 | 2/2011 |
| WO | 2011/023966 A1 | 3/2011 |
| WO | 2012/080382 A1 | 6/2012 |

OTHER PUBLICATIONS

Aqualon Natrosol Physical and Chemical Properties pdf (24 pages); published 1999.*
International Search Report and Written Opinion for PCT/EP2016/056763 dated Jun. 8, 2016.
European Search Report filed in 15164393.9-1460 dated Oct. 14, 2015.

* cited by examiner

*Primary Examiner* — Jeffrey T. Palenik
(74) *Attorney, Agent, or Firm* — Sandra B. Weiss

(57) ABSTRACT

An emulsion stabilizer includes a biopolymer blend of one or more cellulose ether and one or more cross-linked, modified starch wherein one or more of the cellulose ether or the cross-linked, modified starch is hydrophobically modified and wherein the total amount of cellulose ethers in the biopolymer blend is not greater than 50 wt %. The invention further relates to emulsion compositions comprising the emulsion stabilizer, and particularly oil-in-water emulsions. In one embodiment the emulsions are suitable for use in personal care formulations.

15 Claims, 6 Drawing Sheets

Figure 1 Elastic Modulus of Formulations (aqueous phase) at the frequency of 0.2 rad/sec Figure 2 Complex Viscosity of Formulations (aqueous s phase) at frequency of 0.2 rad/sec.

BIOPOLYMER BLENDS AS EMULSION STABILIZERS

FIELD OF THE INVENTION

This application is a national stage filing under 35 U.S.C. § 371 of PCT/EP2016/056763, filed Mar. 29, 2016, which claims priority to U.S. Provisional Patent Application No. 62/141,442 filed Apr. 1, 2015, and European Patent Application No. 15164393.9, filed Apr. 21, 2015, the contents of which are each incorporated herein by reference in their entireties.

The present invention relates to emulsion stabilizers and emulsions including the emulsion stabilizers. More specifically, the present invention relates to emulsion stabilizers comprising biopolymer blends of one or more cellulose ethers and one or more cross-linked, modified starches, wherein one or more of the cellulose ether and the cross-linked, modified starch is hydrophobically modified.

BACKGROUND OF THE INVENTION

Emulsion stability is important to provide long term shelf storage that is needed for commercial emulsions. In the personal care industry, examples of emulsions requiring long-term stability can include certain sunscreens, skin moisturizing formulations, skin creams and hair styling formulations. In these types of personal care formulations, synthetic materials including small molecules have typically been used as emulsifiers. However, certain small molecule emulsifiers may lead to irritation, toxicity, and negative interactions with the cosmetic functional materials in the formulations. In addition, certain small molecule emulsifiers also may not provide the desired long-term emulsion stability.

It is desirable that emulsion stabilizers for personal care compositions be insensitive to salts that may be included in personal care compositions, so that the composition formulator is not unduly constrained in the choice of ingredients to include in a personal care formulation.

Particularly for personal care formulations intended for application to the skin, it is desirable that emulsion stabilizers have tactile qualities that are appealing to the user.

Starches and starch derivatives are known to impart desired tactile qualities to personal care formulations. Starches that are used in such formulations must be at concentrations above about 3%, otherwise the starches can undergo a phenomenon known as retrogradation and precipitate from the formulation.

Cellulose and its derivatives are known to act as emulsifiers, but can impart undesirable tactile qualities when used as emulsifiers in personal care products, particularly for those products intended for application to the skin.

US 2012/0121519 A1, assigned to the common assignee herein, discloses polymeric emulsifiers including polysaccharides modified with one or more cross-linking reagent and with from about 1 mol % to about 10 mol % of one or more ionic reagent, methods for preparing the same, and emulsions including the polymeric emulsifiers.

WO 2009/080657 describes using one or more hydrophobically modified polysaccharide in combination with a fatty acid ester of a polyol to obtain a water-in-oil emulsion that is said to have long-term stability and good sensory properties. The hydrophobically modified polysaccharides described therein include inulins, celluloses and derivatives thereof, starches and agars, and mixtures thereof, and the preferred fatty acid ester of a polyol is polyglyceryl-4 diisostearate/polyhydroxy-stearate/sebacate. As described therein, the oily continuous phase is prepared with the one or more fatty acid ester of a polyol, and the aqueous phase is prepared with the hydrophobically modified polysaccharide, and the two phases are then combined to make a water-in-oil emulsion.

It is one object of the invention to provide emulsion stabilizers that comprise sustainable products, and that provide good long term stability.

It is another object of the invention to provide emulsion stabilizers that provide acceptable tactile qualities when used in personal care formulations.

It is yet another object of the invention to provide emulsion stabilizers that are sufficiently salt-insensitive to facilitate the use of salt compounds in personal care formulations, for example for skin, hair and other personal care applications.

SUMMARY OF THE INVENTION

In a first embodiment, the present invention generally relates to an emulsion stabilizer comprising a biopolymer blend of one or more cellulose ether and one or more cross-linked, modified starch wherein one or more of the cellulose ether and the cross-linked, modified starch is hydrophobically modified.

In an embodiment, the present invention generally relates to an emulsion stabilizer comprising a biopolymer blend of one or more cellulose ether and one or more cross-linked, modified starch wherein the one or more cellulose ether is hydrophobically modified.

In an embodiment, the present invention relates to an emulsion stabilizer comprising a biopolymer blend of one or more cellulose ether and one or more cross-linked, modified starch wherein the one or more cellulose ether is hydrophobically modified and wherein the total amount of cellulose ethers in the biopolymer blend is not greater than 50 wt %.

In another embodiment the invention relates to a method of making an emulsion stabilizer comprising a biopolymer blend of one or more cellulose ether and one or more cross-linked, modified starch, wherein one or more of the cellulose ether and the cross-linked starch is hydrophobically modified.

In another embodiment the invention relates to a method of making an emulsion stabilizer comprising a biopolymer blend of one or more cellulose ether and one or more cross-linked, modified starch, wherein the one or more cellulose ether is hydrophobically modified.

In another embodiment the invention relates to an emulsion formulation comprising a continuous phase, a discontinuous phase, and an emulsion stabilizer, wherein the emulsion stabilizer comprises a biopolymer blend of one or more cellulose ether and one or more cross-linked, modified starch, wherein one or more of the cellulose ether and the cross-linked, modified starch is hydrophobically modified.

In another embodiment the invention relates to an emulsion formulation comprising a continuous phase, a discontinuous phase, and an emulsion stabilizer, wherein the emulsion stabilizer comprises a biopolymer blend of one or more cellulose ether and one or more cross-linked, modified starch, wherein the one or more cellulose ether is hydrophobically modified.

The blends of the invention are called biopolymer blends as they contain as their components one or more cellulose ether and one or more modified starch which cellulose ether and starch components are considered biopolymers.

DESCRIPTION OF THE DRAWINGS

The invention is best understood from the following detailed description when read in connection with the accompanying drawings. Included in the drawings are the following figures.

DETAILED DESCRIPTION OF THE INVENTION

Figure 1:
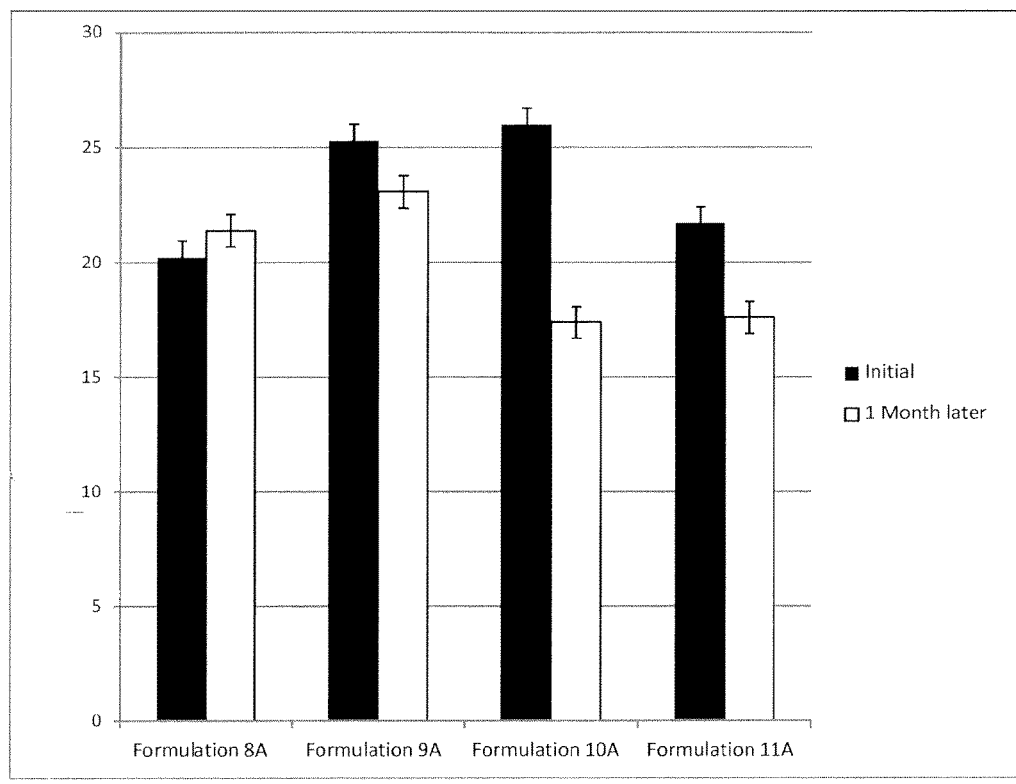
FIG. 1 is a graph of the elastic modulus of the aqueous phase of compositions comprising a hydrophobically modified cellulose ether blended with each of a cross-linked, modified starch; a non-cross-linked, modified starch; and a non-cross-linked, non-modified starch, taken initially and after one-month of storage, in accordance with Example 3.

The present invention relates to emulsion stabilizers comprising sustainable products and providing good long term storage stability.

As used herein, the term "modified" as applied to starch refers to starch molecules that have been reacted at one or more of their hydroxyl groups.

As used herein, the term "hydrophobically-modified" as applied to either cellulose or starch refers to a cellulose or starch molecule that has been substituted with one or more aliphatic or aromatic, saturated or unsaturated, linear, branched or cyclic $C_8$-$C_{30}$ hydrocarbon-based chain(s), in particular hydrophobic group(s) containing from 8 to 30 carbon atoms.

As used herein, the "weight" of any starch or cellulose material is reported on a dry weight basis.

As used herein, the term "long term stability" shall mean stability of an emulsion over a period of at least 28 days, both at room temperature and 45° C., measured using a TURBISCAN® LAB stability analyzer as described in the Examples section herein.

Starch is known to provide desirable tactile properties when used in an emulsion in a personal care composition. It is known, however, that when starch is used as a sole emulsion stabilizer, then a phenomenon called retrogradation can occur which typically results in instability of the emulsion. Such retrogradation is therefore undesired.

In accordance with the invention, a composition comprising a biopolymer blend of a cellulose ether and a cross-linked, modified starch, wherein one or more of the cellulose ether and the cross-linked, modified starch is hydrophobically modified, can act as an efficient emulsion stabilizer composition for oil-in-water emulsions for long-term stability for both hydrocarbon-based oils and natural oils. In one embodiment, a composition comprising a biopolymer blend of a cellulose ether and a cross-linked, modified starch, wherein the one or more cellulose ether is hydrophobically modified, can act as an efficient emulsion stabilizer composition for oil-in-water emulsions for long-term stability for both hydrocarbon-based oils and natural oils. In one embodiment, the weight ratio of the cellulose ether to the cross-linked, modified starch is no greater than about 1:1. Such emulsion stabilizer compositions were found to not suffer from retrogradation, while providing good tactile qualities.

The biopolymer blends of the present invention have particular advantages as emulsion stabilizers in personal care formulations, such as in skin care applications and hair styling applications. For example, in addition to sustainability, the natural tactile qualities provided by the subject biopolymer blends will be appealing compared to tactile qualities of synthetic stabilizers. Also, their substantial salt tolerance will enable formulators to blend in various ingredients. The inventive biopolymer blends exhibit long-term emulsion stability, as measured using the TURBISCAN® LAB stability analyzer and method described in the Examples section herein, using low biopolymer concentrations yet without retrogradation of the starch component.

Cellulose Ethers

Cellulose is a polysaccharide built up from 1,4-anhydroglucose units. The cellulose molecules in native cellulose are insoluble in water. To make cellulose soluble, it has to be modified into a cellulose derivative, such as hydroxyethyl cellulose (HEC), ethyl hydroxyethyl cellulose (EHEC), hydroxylpropyl cellulose (HPC), hydroxybutyl methylcellulose (HBMC), hydroxypropyl methylcellulose (HPMC), methyl ethyl hydroxyethyl cellulose (MEHEC), and hydrophobically modified ethyl hydroxyethyl cellulose (HME-HEC).

To make the modified cellulose, the cellulose is subjected to an alkalization step, and then reacted with ethylene oxide and ethyl chloride to make EHEC, and also with methyl chloride to make MEHEC. The anhydroglucose units of cellulose each have three hydroxyl groups available for reaction. The number of hydroxyl groups per anhydroglucose unit that have reacted is expressed as degree of substitution (DS) and ranges from 0 to 3. The molar substitution of ethylene oxide ($MS_{EO}$) is the average total number of ethylene oxide groups per anhydroglucose unit.

The cellulose ether materials suitable for use in the emulsion stabilizers of the present invention can be derived from any cellulose source, including, but not limited to, hardwood pulp, softwood pulp, cotton sources including cotton linters, bacterial cellulose, and regenerated cellulose.

In one embodiment the cellulose ethers used in the biopolymer blends of the present invention are non-ionic cellulose ethers. In an embodiment, the cellulose ethers are hydroxy($C_1$-$C_4$)alkylcelluloses.

Examples of non-ionic cellulose ethers are methyl cellulose, ethyl cellulose, propyl cellulose, butyl cellulose, hydroxyethyl cellulose, methylhydroxyethyl cellulose, ethylhydroxyethyl cellulose, methylethylhydroxyethyl cellulose, propylhydroxyethylcellulose, hydroxypropylmethyl cellulose, hydroxypropylethyl cellulose, hydroxypropylpropyl cellulose, hydroxypropylhydroxyethyl cellulose, methylhydroxypropylhydroxyethyl cellulose, hydroxypropyl cellulose, and mixtures thereof. In one embodiment, the cellulose ethers used in the biopolymer blends of the present invention include, but are not limited to, methyl cellulose, ethyl cellulose, ethylhydroxyethyl cellulose, methylhydroxyethyl cellulose, methylethylhydroxyethyl cellulose, hydroxypropylmethyl cellulose and mixtures thereof.

In one embodiment, the cellulose ethers used in the biopolymer blends of the present invention are methylethylhydroxyethyl celluloses, referred to herein as "MEHEC".

In one embodiment, the cellulose ethers used in the biopolymer blends of the present invention are ethylhydroxyethyl celluloses, referred to herein as "EHEC".

Suitable non-ionic cellulose ethers include those sold under the trademark Bermocoll® by Akzo Nobel Functional Chemicals, LLC of Chicago, Ill. Other suitable cellulose ethers may include those sold under the mark Natrosol™ hydroxyethylcellulose of Ashland Inc. of Covington, Ky.

Non-ionic cellulose ethers can be of particular utility for those applications in which good salt tolerance is desired.

In one embodiment the cellulose ethers used in the biopolymer blends of the present invention are anionic cellulose ethers, particularly in formulations that do not require high tolerance of salt compounds.

Examples of anionic cellulose ethers are carboxymethyl cellulose, hydroxyethylcarboxymethyl cellulose, hydroxypropylcarboxymethyl cellulose, sulfoethyl cellulose, hydroxyethylsulfoethyl cellulose, hydroxypropylsulfoethyl cellulose, and mixtures thereof.

The cellulose ethers can be prepared according to conventional methods that are known to those of ordinary skill in the art. For example, alkali cellulose (activated cellulose) may be prepared in one or several steps by first mercerizing cellulose with alkali and subsequently reacting the alkali cellulose in one or several steps with appropriate amounts of one or more etherifying agents selected from ethylene oxide, propylene oxide, butylene oxide, methyl chloride, ethyl chloride, monochloro acetic acid (MCA), and salts of MCA, in the presence of an organic reaction medium, for instance ethyl chloride, acetone, alkyl-blocked mono or poly(ethylene glycols), isopropanol, tert-butanol, ethers such as methyl tert.butylether, methyl sec.butylether, dimethoxyethane or mixtures thereof at a temperature in the range of from about 50 to about 120° C.

The cellulose ethers are characterized by the presence of one or more substituents on the cellulose chain.

In one embodiment the cellulose ethers are substituted with hydroxyalkyl such as ethylene oxide, characterized as $MS_{EO}$. In one embodiment the $MS_{EO}$ is at least 1.0, in one embodiment at least 1.5, in one embodiment at least 2.0, in one embodiment at least 2.4.

In one embodiment the cellulose ethers are methyl and/or ethyl substituted in which the sum of $DS_{ethyl}$ and $DS_{methyl}$ is at least 0.1, in one embodiment at least 0.2, in one embodiment at least 0.4, in one embodiment at least 0.6, and in one embodiment at least 0.8.

In one method of making alkyl-substituted cellulose ethers, the cellulose is mercerized in one or several steps with aqueous alkali in a total amount of about 0.8 to about 1.8 moles of alkali per mole of saccharide unit; and the mercerized cellulose is reacted with ethylene oxide in a total amount of about 2.6 to about 5.5 moles per mole of saccharide unit. The reaction product is then reacted with either ethyl chloride in a total amount of about 0.2 to about 1.5 moles per mole of saccharide unit, to make EHEC, or ethyl chloride and methyl chloride in a total amount of about 0.2 to about 1.5 moles per mole of saccharide unit to make MEHEC. These components are added to and reacted with the mercerized cellulose in one or several steps in the presence of an organic reaction medium at a temperature from about 50 to about 120° C. In an embodiment of the invention, the weight ratio between the reaction medium and the cellulose can be about 1:1 to about 10:1, and in another embodiment from about 4:3 to about 3:1.

In one embodiment, methyl chloride or ethyl chloride can serve as both the etherifying agent and the reaction medium, in which case the desired amount of methyl or ethyl chloride is already present in the reaction mixture and there is no need for further addition of methyl or ethyl chloride. The alkylation can be regulated by source of cellulose, the amount of alkali used, the reaction temperature and reaction time. If desired, a part of the alkali may be added at a later stage during the reaction in order to further activate the cellulose. The total degree of substitution by methyl and ethyl can be controlled by the amount of alkali used in the mercerization process, since a corresponding equivalent amount of NaOH is consumed and forms sodium chloride. However, due to side reactions the yield of alkyl substitutions is about 40 to about 60%. U.S. Pat. No. 7,319,146, which is incorporated by reference in its entirety herein, provides a general description of the methods used in making cellulose ether polymers.

One method of making cellulose ethers suitable for use in the present invention is disclosed in U.S. Publication No. 2009/0326217, incorporated herein by reference in its entirety, wherein the cellulose ether is prepared in the presence of an ether-type solvent.

Hydrophobic Modification

In one embodiment, the cellulose ethers may be hydrophobically modified by substitution with one or more aliphatic or aromatic, saturated or unsaturated, linear, branched or cyclic hydrophobic group(s) comprising from 8 to 30 carbon atoms. In one embodiment, the hydrophobic substituent(s) used may include $C_8$-$C_{30}$, and in another embodiment preferably $C_8$-$C_{22}$, alkyl, arylalkyl or alkylaryl groups and mixtures thereof. In an embodiment, the hydrophobic substituent is $C_8$-$C_{22}$, preferably $C_{16}$-$C_{20}$, saturated alkyl chains, such as cetyl ($C_{16}$), stearyl ($C_{18}$) or behenyl ($C_{20}$) groups. In an embodiment, the hydrophobic substituent(s) according to the present invention are cetyl groups or stearyl groups. In an embodiment, the hydrophobic groups are derived from natural sources, such as tall oil, tallow, soy, coco, and palm-oil.

The hydrophobic modifier can be attached to the cellulose ether substrate via an ether, ester or urethane linkage. Preferred is the ether linkage as the reagents most commonly used to effect etherification are readily obtained, the reaction is similar to that commonly used for the initial etherification, and the reagents are usually more easily handled than the reagents employed for modification via the other linkages. The resulting linkage is also usually more resistant to further reactions. In one embodiment the reaction can be accomplished by slurrying the nonionic cellulose ether in an inert organic diluent such as a lower aliphatic alcohol, ketone, or hydrocarbon and adding a solution of alkali metal hydroxide to the resultant slurry at a low temperature, then adding a $C_{10}$ to $C_{24}$ epoxide and continuing with agitation until the reaction is complete.

Hydrophobically modified cellulose ethers and methods for their preparation are known in the art. For example, U.S. Pat. No. 6,627,751 incorporated herein by reference discloses a hydrophobically modified anionic cellulose ether obtainable by a process comprising reacting an alkali metal cellulose not carrying a hydroxyalkyl group with at least three alkylating reagents, wherein one or more of the alkylating reagents is selected from the group of haloacetic acids, alkali metal haloacetates, alkali metal vinyl sulfonates, and vinyl sulfonic acid; one or more of the reagents is of the formula $R^1$—$(OCH_2CH(R^2))_n$—P wherein $R^1$ represents a $C_2$-$C_7$ group, $R^2$ is hydrogen or a methyl group, n is 0-2, and P represents a glycidyl ether group, a 3-halo-2-hydroxypropyl ether group, a 1,2-epoxy group, or a halide; and one or more reagents is of the formula $R^3$—$(OCH_2CH(R^2))_m$—P wherein $R^3$ represents a $C_8$-$C_{30}$ group, m is 0-10, and $R^2$ and P have the meaning as described above. US 2009/0326217, incorporated herein by reference, discloses a process for preparing a cellulose ether wherein the cellulose ether is prepared in the presence of an ether of the formula $R^1$—O—$R^2$ having a boiling point between 40 and 90° C., or of a solvent mixture comprising an ether and having a boiling point between 40 and 90° C., wherein $R^1$ and $R^2$ may be the same or different and are independently selected from an alkyl group, preferably a linear or branched $C_1$-$C_6$ alkyl group.

In one embodiment, the hydrophobically modified cellulose ether includes ethylhydroxyethylcellulose ethers (HM-EHEC). In one embodiment the hydrophobically modified cellulose ether can be hydrophobically modified hydroxyethylcellulose (HM-HEC).

Another factor to be considered is the molecular weight of the hydrophobically modified cellulose ether. Molecular weight can be determined by physical properties such as intrinsic viscosity or by spectrophotometric analysis such as light scattering. For purposes of this invention, all molecular weights are given in weight average molecular weight (Mw) as determined by light scattering methods as are known in the art, and exemplified by the procedure set forth below in the Examples section of this application. The units reported are in Daltons (Da).

In an embodiment of this invention, the molecular weight of the hydrophobically modified cellulose ether will be at least 900,000, more preferably at least 1,000,000. In an embodiment of the invention the molecular weight will be no greater than about 2,000,000, in one embodiment no greater than about 1,500,000, in one embodiment no greater than about 1,200,000.

In another embodiment of this invention, the molecular weight of the hydrophobically modified cellulose ether will be not greater than 900,000, and in one embodiment not greater than 800,000. In an embodiment of the invention the molecular weight will be no less than about 200,000, in one embodiment no less than about 300,000.

Starch

The starch component of the present invention can be isolated from any plant source of starch, including, for example, corn, wheat, rice, sorghum, pea, potato, tapioca (cassava), sweet potato, and sago. In an embodiment of this invention, the starch contains greater than about 90 percent of amylopectin. In another embodiment, the starch contains greater than 95 percent of amylopectin. In yet another embodiment, the starch contains greater than 97 percent of amylopectin.

This high amylopectin starch is traditionally known in the art as waxy and there are many varieties of waxy starch commercially available. In an embodiment of this invention the waxy starch is of corn, rice, potato, or tapioca.

In a preferred embodiment of the present invention, the starches will have a high molecular weight. For purposes of this invention, high molecular weight is defined as the molecular weight of naturally occurring starches which have not been purposefully degraded to a lower molecular weight. That is, while some degradation may occur during the isolation of the starch and also during the chemical processing and drying of the starch, for purposes of the present invention, the high molecular weight starches are those that have their natural molecular weight maintained as much as possible. In another embodiment, the starch may be partially degraded in a controlled fashion by means known in the art including but not limited to acid catalyzed hydrolysis, enzyme catalyzed hydrolysis, and oxidative degradation. In the case where the starch is intentionally partially degraded, the Water Fluidity (WF) of the degraded starch will be less than 70, preferably, less than 60 or, most preferably, less than 45.

Starches suitable for use in the present invention are cross-linked. Cross-linking of the starch chains can be achieved by suitable cross-linking agents, such as bifunctional compounds. In a further embodiment, cross-linking is achieved by reaction of the starch with epichlorohydrin. In a further embodiment, a preferred cross-linking method is phosphorylation, in which the starch is reacted with phosphorous oxychloride, phosphorous pentoxide, and/or sodium trimetaphosphate, such that two starch chains are cross-linked by an anionic P—O group. The anionic character of the cross-linking sites assists the emulsion-stabilizing action of the starch. In a further embodiment, a further preferred cross-linking method is by means of $C_4$-$C_{18}$ alkane or alkene dicarboxylic acids, in another embodiment preferably $C_4$-$C_8$ alkane dicarboxylic acids, and in particular adipic acid. The alkane or alkene dicarboxylic acid links two starch chains via ester bonds. It can be in straight or branched chain form. In a further embodiment, the cross-linked starches are obtained, e.g., by reacting starch with the mixed anhydrides of dicarboxylic acid and acetic acid. The starch may be cross-linked with from about 15 ppm to about 400 ppm of the cross-linking reagent, in another embodiment preferably from about 50 to about 300 ppm, in yet another embodiment more preferably from about 100 ppm to about 200 ppm.

In a further aspect, the cross-linked starch is further modified by addition of a $C_2$-$C_5$ hydroxyalkyl moiety. Without wishing to be bound by theory, it is believed that the presence of a hydroxyl group, which is bound to the starch backbone via an alkyl group with 2 to 5 carbon atoms, leads to a suitable hydrophilic-lipophilic balance of the starch. The position of the hydroxyl group in the alkyl group is not critical and may be in the alpha to the omega positions. The degree of substitution is the average number of substituted OH groups of the starch molecule per anhydroglucose unit. In an embodiment, the degree of substitution of the hydroxyalkylation is preferably approximately 0.08 to 0.3, and in another embodiment, more preferably, the degree of substitution of the hydroxyalkylation is preferably approximately 0.15 to 0.25. The hydroxyalkylation of a native starch can be brought about by reacting a native starch with alkylene oxides with the appropriate number of carbon atoms. In an embodiment, particularly preferred are hydroxyethylated and/or hydroxypropylated starches obtained by reacting starches with ethylene oxide or propylene oxide. A starch to be used according to the invention can also contain more than one hydroxyl group per alkyl group. In an embodiment, a particularly preferred cross-linked, modified starch for the purpose of the present invention is a cross-linked, hydroxypropyl di-starch phosphate or cross-linked acetylated di-starch adipate.

The cross-linked starches of this invention may be hydrophobically modified, and as such, may be substituted with one or more aliphatic or aromatic, saturated or unsaturated, linear, branched or cyclic $C_8$-$C_{30}$ hydrocarbon-based chain(s), in particular hydrophobic group(s) containing from 8 to 30 carbon atoms. In another embodiment, the hydrophobic substituent(s) used may include $C_8$-$C_{30}$, and in another embodiment preferably $C_8$-$C_{22}$, alkyl, alkenyl, arylalkyl or alkylaryl groups and mixtures thereof. In an embodiment, the hydrophobic substituent is $C_8$-$C_{22}$, preferably $C_8$-$C_{12}$, alkenyl chains, such as octenyl (unsaturated $C_8$) and linear or branched dodecenyl (unsaturated $C_{12}$) groups. In an embodiment the hydrophobic groups are derived from natural sources, including without limitation tall oil, tallow, soy, coco, and palm-oil. In an embodiment, the hydrophobic substituent(s) according to the present invention are octenyl or dodecenyl groups. The hydrophobic modifier can be attached to the starch substrate via an ether, ester or urethane linkage. Preferred is the ester linkage. Exemplary modifying reagents include but are not limited to octenyl succinic anhydride and dodecenyl anhydride.

In an embodiment, the cross-linked, modified starch to be used according to the invention is gelatinized. For purposes of the present invention, the term "gelatinized starch" encompasses "pregelatinized starch," "prepasted starch" and "cold water swelling starch." The term "gelatinized" starch relates to swollen starch particles that have lost their birefringence crosses in polarized light. Gelatinized modified starches are soluble in cold water without cooking. In this context "soluble" does not necessarily mean the formation of a true molecular solution and instead also means that a colloidal dispersion is obtained. The cross-linked, modified starch to be used according to the invention is preferably completely gelatinized.

The modified granular starch may be gelatinized by cooking in water above the gelatinization temperature. Some non-limiting examples of gelatinization are bath cooking, steam injection cooking, jet cooking (at pressures of about 10 to about 150 PSI) and extrusion. It is believed that by gelatinizing the granular starch, the functionality as a component of an emulsion stabilizer is obtainable. The starch of this invention can be cooked at a variety of temperatures and concentrations to provide the functional colloidal suspension. In an embodiment of this invention, the starch is cooked at about 90° C. to about 200° C. In another embodiment, the starch is cooked at about 100° C. to about 150° C. Depending on the method of cooking, limitations on the concentration of starch in water will vary due to factors, for example, such as viscosity, heat transfer and solution stability. In an embodiment of this invention, the starch will be cooked at concentrations from about 1 to about 40 percent by weight (wt %); in another embodiment, the starch will be cooked at concentrations from about 2 wt % to about 30 wt %; and in yet another embodiment from about 3 wt % to about 15 wt %, or yet still other embodiments that are defined by combinations of the upper and lower limits of these ranges.

Processes normally used for producing such gelatinized starches include, inter alia, drum drying, extrusion and spray drying.

Drum drying includes the simultaneous cooking and drying of a very high viscosity, semi-solid starch paste on heated drums. The dried films are stripped from the drum with a metal blade and then ground. This process can be carried out up to a very high solids content.

It is also possible to use extrusion for the simultaneous cooking and drying of starches (c.f. U.S. Pat. No. 3,137,592, which is incorporated by reference in its entirety herein). This process makes use of the physical processing of a starch/water mixture at elevated temperatures and pressures which brings about the gelatinization of the starch, followed by expansion after leaving the nozzle with sudden evaporation of the water.

The use of a gelatinized cross-linked, modified starch allows the starch to be produced at ambient temperature or at a temperature which is considerably lower than the production conditions used for known starch-containing compositions. In an embodiment, preferably the gelatinized cross-linked, modified starch is produced by spray drying.

In an embodiment, the cross-linked, modified starch to be used according to the invention has a majority of intact starch granules. Aqueous dispersions of gelatinized cross-linked, modified starches having a largely intact granular structure have a more uniform smooth texture than aqueous dispersions of starches without a granular structure, which are, e.g., obtained by drying starch solutions whose dispersions have a slightly gritty feel. In the case of gelatinized starches with an intact granular structure, the native internal structure of the hydrogen bonds is destroyed, but the external shape or form is maintained.

A process for producing particularly suitable, spray dried, gelatinized starches is described in U.S. Pat. No. 4,280,851, which is incorporated by reference in its entirety herein. An apparatus adapted for carrying out the process is described in U.S. Pat. No. 4,600,472, which is also incorporated by reference in its entirety herein. In this process a mixture of the granular starch or modified starch is cooked or gelatinized in the atomized state. The starch to be cooked is atomized through an atomizing opening into a nozzle arrangement in order to form a relatively finely divided sprayed material. In addition, a heating medium is injected through an opening in the nozzle arrangement into the sprayed material so as to heat the starch to the temperature necessary for gelatinization. A closed chamber surrounds the injection openings for the atomizing and heating medium and defines a ventilation opening positioned in such a way that the heated starch spray material can leave the chamber. The arrangement is such that during the passage of the starch spray material through the chamber, i.e., from the atomizing opening to the ventilation opening, the time elapsed defines the starch's gelatinization time. The resulting spray dried, gelatinized starch includes uniformly gelatinized starch granules in the form of indented spheres, most of the granules being whole and unbroken and swollen after hydration. Nozzles usable for producing such starches are also described in U.S. Pat. No. 4,610,760, which is incorporated by reference in its entirety herein.

For the production of suitable gelatinized starches or modified starches it is also possible to use the process of U.S. Pat. No. 5,149,799, which is incorporated by reference in its entirety herein. In this process starch is uniformly atomized and cooked by means of a single atomization stage in the presence of an aqueous medium. The atomization stage is performed in an apparatus having an internal mix two-fluid spray drying nozzle and it is coupled to a device for drying the cooked, atomized starch.

Spray dried, gelatinized starches or modified starches with suitable characteristics can also be produced by a continuous, coupled jet-cooking and spray-drying process. A starch suspension is gelatinized at 138° C. to 160° C. in a jet cooker with direct steam injection. The streams of starch suspension and steam are mixed in a cooking or boiling chamber. The outlet of the latter is connected to a pneumatic spray nozzle or a high pressure nozzle, which is located in a conventional spray dryer. The jet-cooked starch is directed at elevated temperature and pressure into the spray nozzle and can be atomized with cold air, hot air or preferably steam. After atomizing, the hot, jet-cooked starch solution is handled in the same way as conventional spray dried starches. The drying process is adequately fast to prevent retrogradation of the starch molecules during the cooling and drying of the droplets. The spray dried starch is an amorphous material (i.e., it is substantially non-crystalline) which is easily soluble in water or colloidally dispersible.

In an embodiment, the cross-linked, modified starch according to the invention can be provided as a dry powdery composition which is reconstituted in an aqueous medium upon use.

The cross-linked, modified starches suitable for use according to the invention have use characteristics and tactile qualities that are dermatologically desirable. They increase the water retention capacity of the skin, and help make the skin smooth and flexible. Cosmetics containing emulsion stabilizers of the present invention with the cross-linked, modified starch can be spread very well onto the skin and do not leave behind a sticky feeling.

Biopolymer Blends

In another aspect, the invention provides a method for making emulsion stabilizers. The method comprises blending a cellulose ether with a cross-linked, modified starch to make a biopolymer blend, wherein one or more of the modified cellulose ether and the cross-linked, modified starch is hydrophobically modified. In an embodiment, the method may include cross-linking a starch with one or more cross-linking reagent and further modifying the cross-linked starch, for example by hydroxyalkylation prior to blending the cross-linked, modified starch with a hydrophobically modified cellulose ether. In another embodiment, the method comprises hydrophobically modifying the cellulose ether or the cross-linked modified starch with one or more hydrophobic reagent prior to blending the cellulose ether and starch components.

In an embodiment, the total amount of cellulose ethers in the biopolymer blend is not greater than 50 wt %. In one embodiment the total amount of cellulose ethers in the blend is at least about 5 wt %, in one embodiment at least about 10 wt %, in one embodiment at least about 20 wt %. In one embodiment the total amount of cellulose ethers in the blend is no greater than about 45 wt %, in one embodiment no greater than about 40 wt %, in another embodiment no greater than about 30 wt %, in another embodiment no greater than about 25 wt %.

Emulsified Personal Care Formulations

Generally, an emulsion comprises a mixture of two immiscible liquid substances, one substance (the dispersed phase) dispersed in the other (the continuous phase). For the purposes of this invention, an emulsion is defined as a plurality of oil droplets substantially uniformly distributed or dispersed in a liquid medium. Usually the emulsion is in this form at room temperature. For some oils with a solidification point at a temperature below 100° C. the emulsion can also be a formulation wherein the oil was first dispersed in water, but upon cooling to room temperature the oil may have solidified to a certain extent. The liquid medium forms the continuous phase, and the oil is not soluble in the liquid medium. In an embodiment the solubility in the liquid medium is 0.1% by weight, preferably 0.05% by weight, or lower. Some non-limiting examples of suitable liquid media include water, ethanol, methanol, isopropanol, glycerol, propylene glycol, or acetone or mixtures thereof. In an embodiment of the invention, the liquid medium is a mixture of water with one or more of ethanol, methanol, isopropanol, glycerol, glycols, such as propylene glycol, or acetone.

In an aspect, the emulsion stabilizers of the invention can be used to form emulsions including a cosmetically acceptable oil dispersed in water or a water-based medium.

In another aspect, the invention provides an emulsion comprising the emulsion stabilizer; surfactant; a cosmetically acceptable oil; and water or a water-based liquid medium, wherein water or water-based liquid medium is the continuous phase.

In one embodiment of the invention the emulsion is a personal care composition. In one embodiment of the invention the personal care composition is a skin care composition. In one embodiment of the invention the personal care composition is a hair care or hair styling composition. In one embodiment of the invention the emulsion is a hair styling composition selected from a gel, a mousse, a pomade, and a wax.

In one embodiment of the invention the emulsion is a personal care composition selected from the group consisting of a skin care composition, skin cleansing composition, make-up, facial lotion, cream moisturizer, body wash, body lotion, foot care products like foot cream, hand cream, lipstick, lip gloss, lip pencil, eyeshadow, gel eye color, eye liner, eye pencil, mascara, concealer, foundation, facial powder, liquid rouges, blush, deodorant, shaving cream composition, nail polish, gel polish removers, cuticle remover, cuticle cream, acne cream, acne cleansing scrub, toothpaste, shaving lotion, cream depilatory, lotion depilatory, wax depilatory, facial mask made with clay materials, anti-aging product, shampoo, hair care products like conditioner, hair treatment cream, styling gel, styling foam, hair mousse, hair spray, set lotion, blow-styling lotion, hair color lotion and dyes, hair bleaching cream hair relaxing composition, curl activator gel, fragrant hair gloss, sun care products like sun stick and sun screen, soap, handwash, hand sanitizer gels, antibacterial hand cleaner, body scrub, hand scrub, bubble bath, bath oils, instant hand sanitizer, baby lotion, diaper rash cream, wet wipe, baby bath, and vitamin creams.

In an embodiment of this aspect of the invention, the oil is present as at least 10% of the emulsion, in another embodiment at least 20% of the emulsion, in still another embodiment at least about 30% of the emulsion. In one embodiment of this aspect of the invention, the oil is present as no more than 50% of the emulsion, in yet another embodiment no more than 40% of the emulsion.

In an embodiment of the invention, the oil droplets in the emulsion have a mean average particle size of from about 0.2 microns to about 100 microns. In another embodiment, the oil droplets have a mean average particle size of from about 0.5 microns to 35 microns. In yet another embodiment, the oil droplets have a mean average particle size of from about 1 micron to about 25 microns. In embodiments of the invention, the mean average particle size can have lower limits of 0.2 microns, 0.5 microns and 1 micron, respectively, while the upper limits can be 100 microns, 35 microns and 25 microns, respectively, with embodiments having ranges being combinations of these lower and upper limits. Mean average particle size can be measured, for example, by light scattering techniques such as are known to those skilled in the art.

In an embodiment of the invention, the cosmetically acceptable oil is an oil that is not soluble in the solvent system and provides some benefit to the consumer such as feel, protection, healing, UV protection, occlusion, slip, hydration, or radical scavenging. The cosmetically acceptable oil can be selected from hydrocarbon-based oils and natural oils. Non-limiting examples of cosmetically acceptable oils are palm oil, mineral oil, petroleum jelly, petrolatum, silicone, dimethicone, emu oils, castor oils, squaline, avocado oil, almond oil, coconut oil, cocoa butter, grapeseed oil, lanolin, peanut oil, sesame oil, jojoba oil, olive oil, silicone oil, sunflower oil, safflower oil, shea butter, and wheat germ oil.

In an embodiment of the invention, the cosmetically acceptable oil may be an aerosol propellant.

In an embodiment, of the present invention, the usage level of the emulsion stabilizer in the final formulation, for example a skin care formulation or a hair care formulation, can be from about 1 wt % to about 5% wt %. The usage level of the emulsion stabilizer may be selected based in part on the weight average molecular weight of the cellulose ether component of the blend. In an embodiment in which the cellulose ether is a hydrophobically modified cellulose ether having a molecular weight of at least about 900,000, the usage level of the emulsion stabilizer is preferably from about 1 wt % to about 3 wt %, and in yet another embodiment more preferably from about 1.5 wt % to about 2.5 wt %, in yet another embodiment about 2 wt %, based on the total weight of the emulsion formulation. In an embodiment in which the cellulose ether is a hydrophobically modified cellulose ether having a molecular weight of less than 900,000, the usage level of the emulsion stabilizer is preferably from about 3 wt % to about 6 wt %, and in yet another embodiment more preferably from about 4 wt % to about 5.5 wt %, in yet another embodiment about 5 wt %, based on the total weight of the emulsion formulation.

Preservatives are often used in personal care formulations to provide long term shelf stability, particularly microbiological shelf life stability. Suitable preservatives include, for example, methylparaben, propylparaben, butylparaben, DMDM hydantoin, imidazolidinyl urea, gluteraldehyde, phenoxyethanol, benzalkonium chloride, methane ammonium chloride, benzethonium chloride, benzyl alcohol, chlorobenzyl alcohol, methylchloroisothiazolinone, methylisothiazolinone, sodium benzoate, chloracetamide, triclosan, iodopropynyl butylcarbamate, sodium pyrithione, zinc pyrithione, and other cosmetically acceptable preservatives known to those skilled in the art.

Various other additives and active and functional ingredients may be included in the cosmetic composition as defined herein. These include, but are not limited to, emollients, humectants, thickening agents, surfactants, UV light inhibitors, fixative polymers, pigments, dyes, colorants, alpha hydroxy acids, aesthetic enhancers such as starch, perfumes and fragrances, film formers (water proofing agents), antiseptics, antifungal, antimicrobial and other medicaments and solvents.

Surfactants which are useful in this invention include non-ionic and amphoteric surfactants. Non-ionic surfactants which may be used include polyoxyethyleneated, polyoxypropyleneated or polyglycerolated alcohols, alkylphenols and fatty acids with a linear fatty chain containing 8 to 22 carbon atoms and usually 2 to 30 mols of ethylene oxide, fatty acid amides, alkoxylated fatty alcohol alcohol amines, fatty acid esters, glycerol esters, alkoxylated fatty acid esters, sorbitan esters, alkoxylated sorbitan esters, alkylphenol alkoxylates, aromatic alkoxylates and alcohol alkoxylates. Also useful are copolymers of ethylene oxide and propylene oxide, condensates of ethylene oxide and propylene oxide with fatty alcohols, polyoxyethyleneated fatty amides or amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

In addition to personal care formulations, the emulsion stabilizers of this invention can also be used for a variety of industries and applications. Examples of such industries include as an aid in oil well drilling, laundry applications, crop protection, agriculture preparations, asphalt stabilizer, or coating aid.

The present invention will now be illustrated by the following non-limiting Examples. In the Examples the cellulose ethers used are hydrophobically modified ethylhydroxyethyl cellulose products, although the invention is not intended to be so limited, and those skilled in the art will understand from the teachings herein how to adapt these methods to prepare solutions and emulsions using other hydrophobically modified cellulose ethers.

EXAMPLES

Emulsion Preparation Procedure

Emulsions were prepared according to the following representative preparation procedures; those skilled in the art will understand how to adjust the amounts of each of the reagents for other concentration levels and quantities that may be desired.

a. HM-EHEC mother solution preparation (4 wt %)
   Weigh 2 grams of hydrophobically modified ethylhydroxyethyl cellulose ether (HM-EHEC) and slowly disperse into 48 grams water at ambient temperature while mixing using flat blade at 400 rpm with over-head mixer.
   After addition of HM-EHEC, start heating up the aqueous mixture. Start the timer for 15 min once at temperature of 75° C. Reduce the speed to 250-300 rpm as the solution thickens.
   Compensate for the lost water and add preservative.
   Stir more for few min at ambient temperature.

b. Cross-linked, modified starch mother solution preparation (6 wt %)
   Weigh 3 grams of modified starch and slowly disperse the modified starch into 47 grams water at ambient temperature while mixing using flat blade at 400 rpm with over-head mixer.
   After addition of modified starch, start heating up the aqueous mixture. Start the timer for 15 min once at temperature of 90° C. Reduce the speed to 250-300 rpm as the polymer solution thickens. Compensate for the lost water and add preservative. Stir more for few min at ambient temperature.

c. Emulsion (Example of 0.75% HM-EHEC and 1.25% Modified Starch with 30% oil):
   Into a 4 oz. glass jar, weigh out the followings in sequence: 0.5449 gram of SPAN® 80 surfactant, 0.2496 gram of TWEEN® 40 surfactant; 0.49655 gram of Glydant® preservative, 28.9159gram deionized water and 29.7931 gram oil.
   Homogenize the mixture at 13,500 rmp using Ultra Turrax® T25 by IKA WERKE with mixing head S25N -25F dispersing element for 120 sec. Leave 30.2083 gram of homogenized mixture in the jar.
   On top of the jar with homogenized mixture, set up a mixing process using the flat blade stirrer on the emulsion and stir at about 300 rpm using the over-head mixer.
   Add 9.3750 gram of mother solution of HM-EHEC (4wt %), and 10.4167 gram of mother solution of modified starch (6wt %) prepared in a. and b. Mix for additional 10 min at 300 rpm.

The total emulsion is about 50 gram for further evaluation.

Emulsion Stability

For purposes of the present invention, emulsion stability was quantitatively measured using a TURBISCAN® LAB stability analyzer. The analyzer was used to obtain an initial backscattering signal for each sample emulsion formulation. Then, the emulsion formulations were stored at 45° C., and were scanned periodically over the course of about a month. The backscattering signals as measured over time were compared with the signals of the initial samples. More specifically, if the maximum difference of a subsequent backscattering signal relative to the initial signal was larger than 5%, the days to reach this 5% difference in backscattering signal were recorded as a measure of the stability, or "Turbiscan® Time." The longer this time was, the more stable the emulsion. This technique is able to detect potential instability of a sample well before such instability can be visually observed.

Rheology of Aqueous Phase

The stability was also checked by monitoring aqueous phase rheological behavior, which is an indicator of potential retrogradation of polysaccharides blends. Since retrogradation is more severe at lower temperature, sample aqueous solutions were aged at room temperature (at about 20° C.). The rheology of the aqueous solutions was measured over the course of one month to monitor the potential retrogradation. It is believed that aqueous phase rheological properties and the microscopic structures these properties reflect play an important role in emulsion stability. (See Russel, W. B., Saville, D. A., and Schowalter, W. R. (1989), "Colloidal Dispersions" (Cambridge Monographs on Mechanics), Cambridge University Press, Cambridge, UK).

Two types of rheological tests were conducted. Oscillatory rheological measurements were conducted at 20° C., with strain of 5%. The frequency was varied from 0.1 rad/sec to 100 rad/sec. The values of elastic modulus and complex viscosity at 0.2 rad/sec were reported. Shear viscosity measurements were conducted at 20° C., with the shear rate varied from about 0.1 rad/sec or 0.2 rad/sec to 100 rad/sec. The rheometer used was Rheometrics rheometer (Rheometric Scientific, Model # SR-5000).

Molecular Weight Determination of Modified Cellulose Ethers a. MEHEC

Instrument: GPCmax equipped by Tetra Detector Array (TDA 502), both by Malvern

Mobile phase: 0.05 M Na Acetate; 0.02 wt % Sodium Azide; pH 6 (Acetic Acid)

Column: 2×TSK GMPWXL 7.8×300 mm+pre column (Tosoh Bioscience)

Flow : 0.5 ml/min

Injection volume: 100 μl

Column temperature: 35° C.

Detection: Refractive Index, Light Scattering (7° and 90°) and Viscosity

Applied dn/dc: 0.148

All samples were dissolved in mobile phase, shaken overnight and filtered through a 0.45 μm syringe filter (regenerated cellulose membrane, GE Healthcare) prior to SEC analysis. Typical concentration was 0.5 -1 mg/ml.

Narrow MWD Pullulan standard (Mn=100000, Mw=112000, IV=0.458 dl/g, dn/dc=0.144, Shodex) was used to calibrate the detectors. The dn/dc (factor necessary to calculate MWD) was set to 0.148, value typical for cellulose ethers.

b. HM-EHEC

The same as for EHEC, with exception of mobile phase where 0.5 wt % of RAMEA was added to 0.05 M Na Acetate; 0.02 wt % Sodium Azide; pH 6 (Acetic Acid). RAMEA stands for randomly methylated cyclodextrin alpha (Cyclolab).

Example 1

Effect of Molecular Weight on Emulsion Stability

Experiments were conducted to determine the effect of molecular weight of hydrophobically modified ethylhydroxyethyl cellulose (HM-EHEC) on emulsion stability. 1.5% of crosslinked, hydroxylpropyl modified waxy potato starch, or Starch Type "A", was blended with each of three different hydrophobically-modified EHEC samples at 0.5% level as shown in Table 1. Each of the three different hydrophobically modified EHEC samples had $MS_{EO}$ of at least 2.4 and $DS_{ethyl}$ of at least 0.8. Each formulation also contained 0.25% Tween® 40 (a nonionic ethoxylated (20) sorbitan ester surfactant, available from Croda Inc., Edison, N.J.) and 0.55% Span® 80 (a nonionic sorbitan oleate surfactant available from Croda Inc., Edison, N.J.). 30% triglyceride-based oil in the form of safflower oil, and 0.5% Glydant® (a preservative available from Lonza, Inc., Allendale N.J.), the balance water. The data in Table 1 shows that the HM-EHEC with molecular weight of greater than 1,000,000 gave better emulsion stability performance.

TABLE 1

Impact of Molecular Weight of HM-EHEC on Stability of HM-EHEC/Modified Starch Stabilized Safflower Emulsions

| | Modified cellulosic used | Weight average molecular weight of HM-EHEC | Stability (d) |
| --- | --- | --- | --- |
| Formulation 1 | HM-EHEC 1 | 1,100,000 | >28 |
| Formulation 2 (Comparative) | HM-EHEC 2 | 800,000 | 12 |
| Formulation 3 (Comparative) | HM-EHEC 3 | 300,000 | 2 |

Example 2

Impact of Starch Modification—Compatibility with Water

Samples of the hydrophobically modified EHEC denominated HM-EHEC 1 as used in Formulation 1 were blended with each of four different types of starches, and the blends were used to prepare emulsions that also contained 0.2% Tween 80, 30% tetradecane, 0.5% of Glydant® preservative, and the remainder water. The data in Table 2 shows that the cross-linked, modified starch provided superior long term emulsion stability compared to the unmodified, non-cross-linked starches.

TABLE 2

Stability of HM-EHEC/Starch Blend Stabilized Tetradecane Emulsions

| Emulsion | Starch Type | HM-EHEC 1 | Starch | Stability (days) |
|---|---|---|---|---|
| Formulation 4 | A | 0.75% | 1.25% | >28 |
| Formulation 5 (Comparative) | B | 0.75% | 1.25% | 19 |
| Formulation 6 (Comparative) | C | 0.75% | 1.25% | 13 |
| Formulation 7 (Comparative) | D | 0.75% | 1.25% | 14 |

A = cross-linked, hydroxylpropyl modified waxy potato
B = un-modified tapioca starch
C = un-modified waxy potato
D = un-modified waxy corn

Example 3

The Impact of Starch Modification—Cross-linking

Samples of the hydrophobically modified EHEC denominated HM-EHEC1 as used in Formulation 1 were blended with different types of starches and in different proportions, as shown in Table 3, and the blends were used to prepare emulsions that also contained 0.2% Tween 80, 30% tetradecane, 0.5% of Glydant® preservative, and the remainder water. Formulation 8 is a composition of the present invention, and Formulations 9-11 are comparative examples. The data in Table 3 demonstrates that the biopolymer blends of higher viscosity hydrophobically modified cellulose ether with cross-linked, modified starch and wherein the total amount of cellulose ethers in the biopolymer blend is not greater than 50 wt % provided good long term stability. In comparison, the biopolymer blends of the same hydrophobically modified cellulose ether with the same cross-linked, modified starch but wherein the total amount of cellulose ethers in the biopolymer blend is greater than 50 wt % did not provide adequate long term stability. Biopolymer blends of the same hydrophobically modified cellulose ether with starches that were not both cross-linked and modified likewise did not provide adequate long term stability.

TABLE 3

Stability of HM-EHEC/Starch Blend Stabilized Tetradecane Emulsions

| | HM-EHEC 1 | Starch type | Starch | Stability (d) |
|---|---|---|---|---|
| Formulation 8 | 0.75% | A | 1.25% | >28 |
| Formulation 9 (Comparative) | 1.2% | A | 0.3% | 17 |
| Formulation 10 (Comparative) | 1.2% | E | 0.3% | 6 |
| Formulation 11 (Comparative) | 1.2% | D | 0.3% | 6 |

A = cross-linked, hydroxylpropyl modified waxy potato
D = un-modified waxy corn
E = hydroxylpropyl modified waxy corn without cross-linking Compositions were prepared corresponding to the aqueous phase of each of Formulations 8-11. These aqueous compositions are named as Formulation 8A-11A, respectively, and listed in Table 3A.

TABLE 3A

Aqueous solutions corresponding to aqueous phase of Formulations 8-11

| | HM-EHEC1 | Starch type | Starch | Water | Glydant |
|---|---|---|---|---|---|
| Formulation 8A | 1.07% | A | 1.79% | 96.42% | 0.72% |
| Formulation 9A (Comparative) | 1.72% | A | 0.43% | 97.13% | 0.72% |
| Formulation 10A (Comparative) | 1.72% | E | 0.43% | 97.13% | 0.72% |
| Formulation 11A (Comparative) | 1.72% | D | 0.43% | 97.13% | 0.72% |

Figure 2:
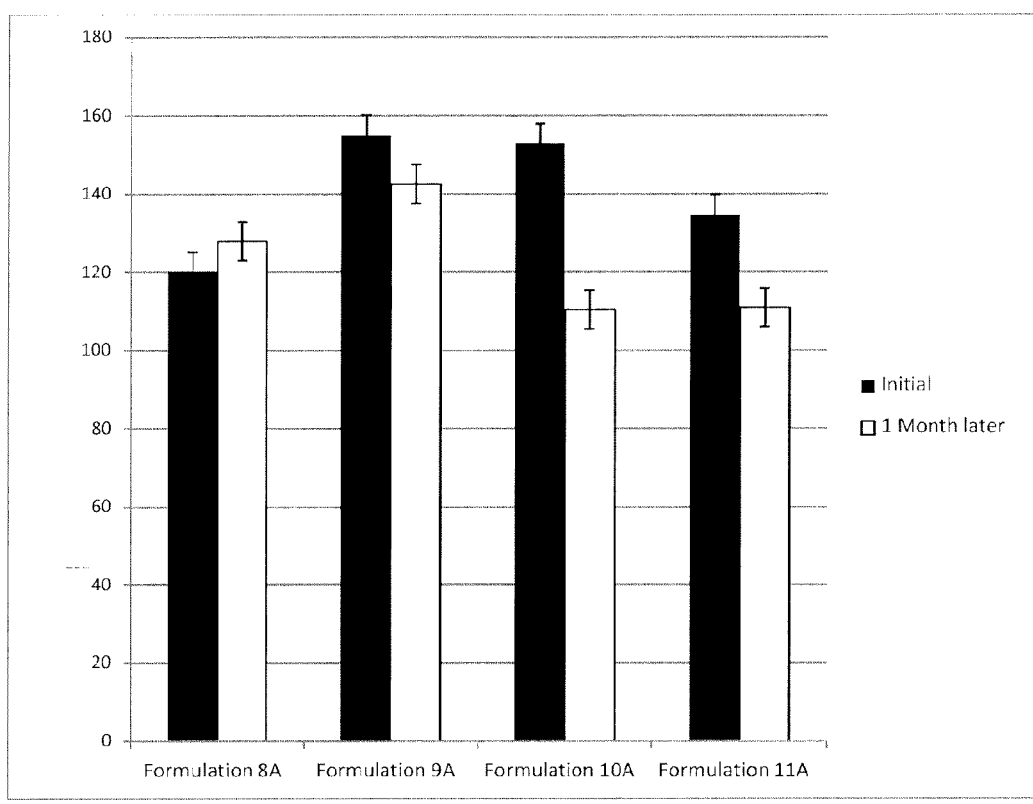
FIG. 2 is a graph of complex viscosity of the aqueous phase of the same compositions that are the subject of FIG. 1, taken initially and after one-month of storage, in accordance with Example 3.

A = crosslinked, hydroxylpropyl modified waxy potato
D = un-modified waxy corn
E = hydroxylpropyl modified waxy corn without crosslinking The rheology of aqueous Formulations 8A-11A was measured by the above-described procedure both when the formulations were initially prepared and again after one month of storage at temperature of 22° C. FIG. 1 illustrates the change in elastic modulus of formulations listed in Table 3A. The oscillation frequency was 0.2 radius/sec. FIG. 2 illustrates the change in complex viscosity of formulations listed in Table 3A. The oscillation frequency was 0.2 radius/sec. These figures demonstrate the minimal change of rheological properties over time when HM-EHEC 1 is blended with cross-linked, modified starch as in Formulation 8A and 9A. Formulations 10A and 11A which used starches that were not both modified and cross-linked showed the greatest change in rheological properties.

Example 4

Triglyceride-based emulsion stability

Samples of the hydrophobically modified EHEC denominated HM-EHEC1 as used in Formulation 1 were blended with cross-linked, modified starch in three different proportions, and the blends were used to prepare emulsions that also contained 0.25% Tween® 40 (a nonionic ethoxylated (20) sorbitan ester surfactant, available from Croda Inc., Edison, N.J.), 0.55% Span® 80 (a nonionic sorbitan oleate surfactant available from Croda Inc., Edison, N.J.), 30% triglyceride-based oil in the form of safflower oil, 0.5% Glydant® preservative, and the balance water. In each Formulation the weight ratio of hydrophobically modified cellulose ether to modified, cross-linked starch was not greater than about 1:1. The data in Table 4 demonstrates that the blends of HM-EHEC 1 and the cross-linked, modified Starch A provided excellent emulsion stability for the triglyceride-based (i.e. safflower oil) emulsions.

TABLE 4

Stability of HM-EHEC/Starch Blend Stabilized Triglyceride Oil Emulsions.

| | HM-EHEC 1 | Starch A | Stability (d) |
|---|---|---|---|
| Formulation 12 | 0.75% | 1.25% | >28 |
| Formulation 13 | 0.85% | 1.15% | >28 |
| Formulation 14 | 1.00% | 1.00% | >28 |

Example 5

Salt Sensitivity of Emulsions Containing Modified Poly-saccharides Blends

Figure 3:
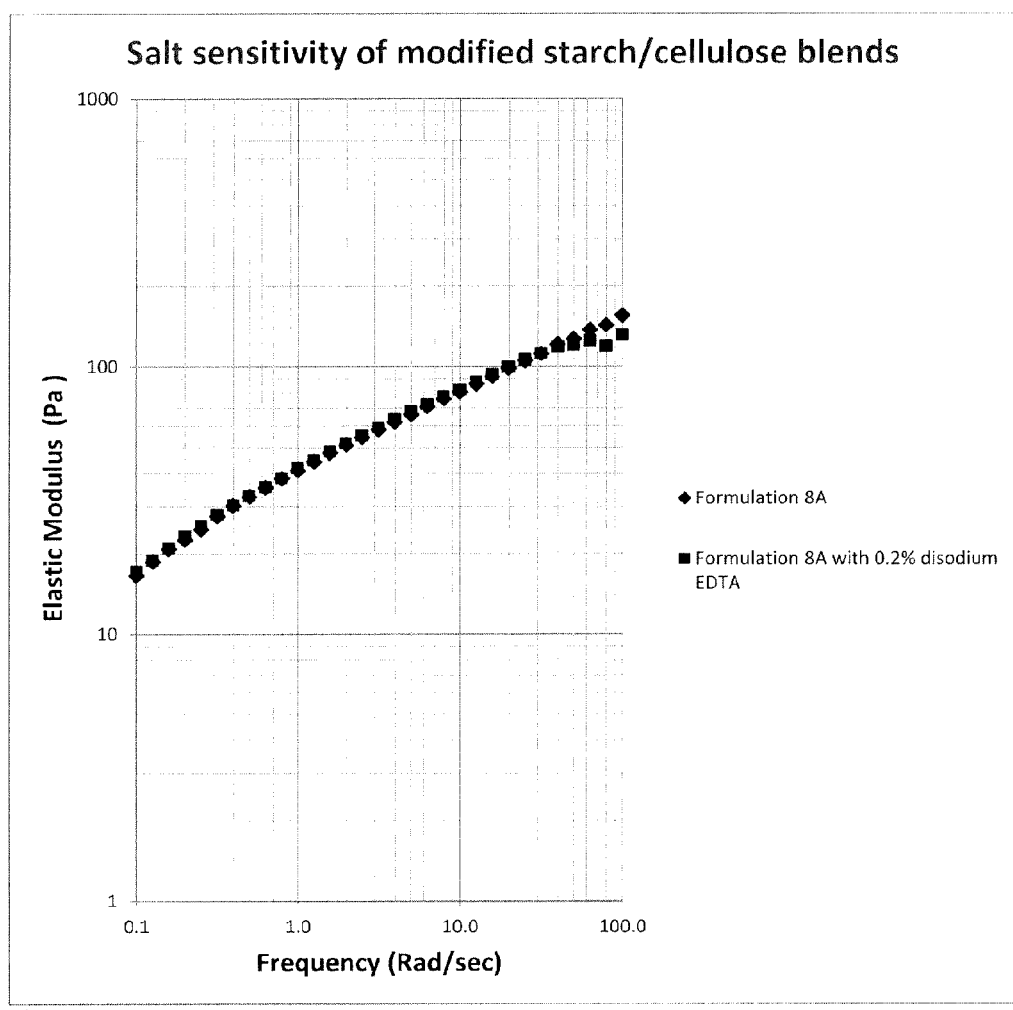
FIG. 3 is a graph illustrating salt sensitivity (measured by elastic modulus) of compositions comprising a hydrophobically modified cellulose ether blended with a cross-linked, modified starch in an aqueous solution, with and without added 0.2% disodium EDTA, in accordance with Example 5.
Figure 4:
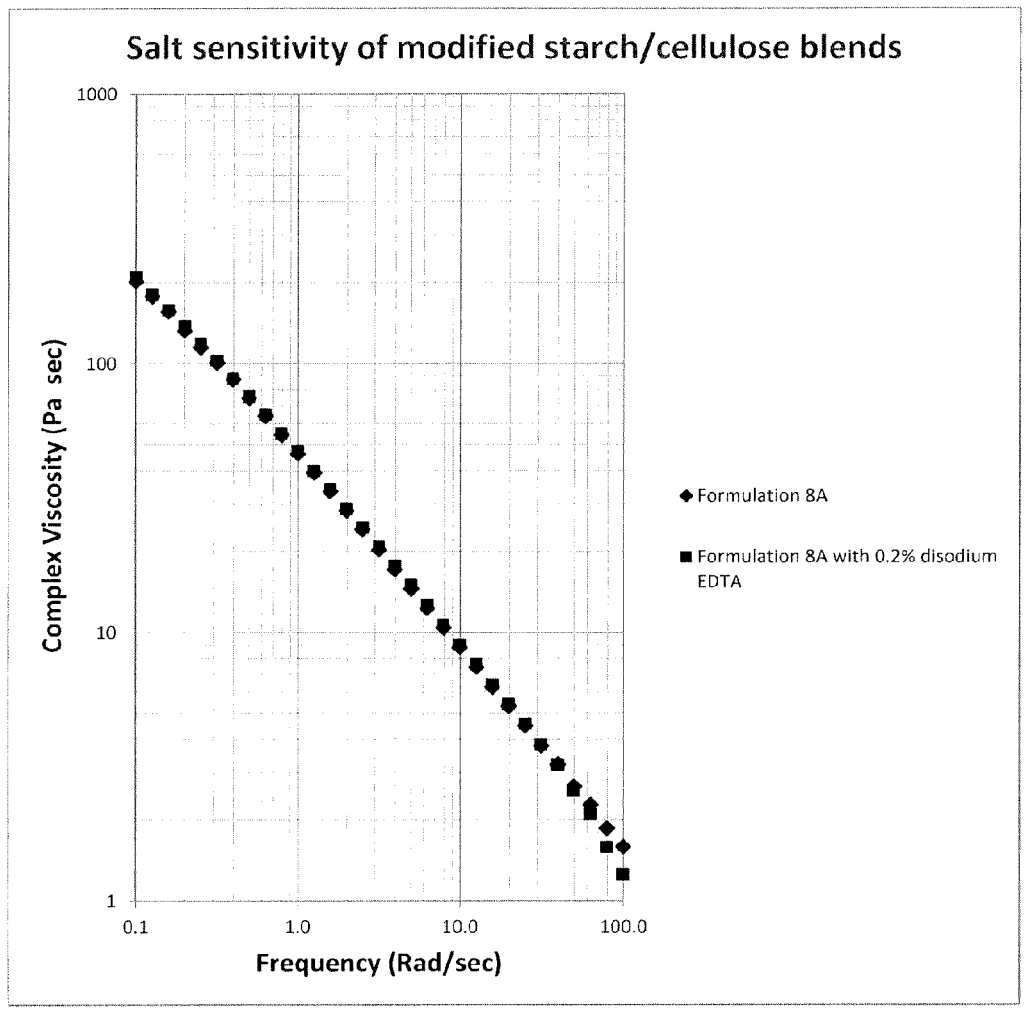
FIG. 4 is a graph illustrating salt sensitivity (measured by complex viscosity) of the same compositions that are the subject of FIG. 3, in accordance with Example 5.

Experiments were conducted to determine if the presence of cosmetically acceptable salts commonly used in personal care formulations would affect the rheological properties of aqueous solutions of the emulsion stabilizers of the present invention. FIG. 3 and FIG. 4 each show the salt sensitivity of aqueous solutions of polymer blends of HM-EHEC 1 and Starch A, in Formulation 8A in Table 3A. 0.2% of disodium EDTA is added in the solution composition. As shown in these charts, the rheology of the polymer solution is insensitive to the addition of salt, in this specific case, disodium EDTA. FIG. 3 shows a variation of elastic modulus of Formulation 8A with and without disodium EDTA. FIG. 4 shows a variation of complex viscosity of Formulation 8A with and without disodium EDTA. The data of FIGS. 3 and 4 indicate that, advantageously, the presence of 0.2% of disodium EDTA did not significantly affect either the elastic modulus or the complex viscosity of the Formulations.

Figure 5:
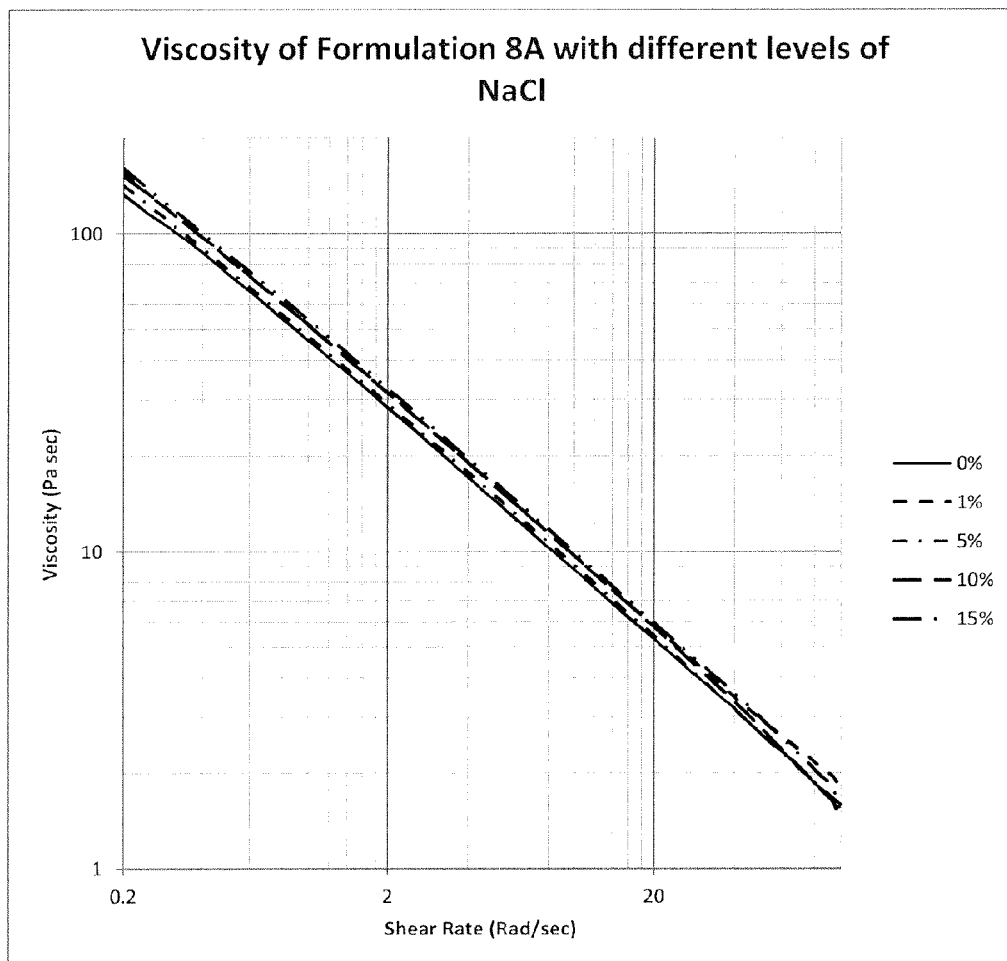
FIG. 5 is a graph illustrating salt sensitivity (measured by shear viscosity) of a composition comprising a biopolymer blend of the present invention in an aqueous solution charged with various levels of NaCl, in accordance with Example 5.

Further experiments were conducted to determine whether other concentration levels of salt would affect the rheological properties of aqueous solution comprising emulsion stabilizers of the present invention. Samples of formulation 8A were prepared as above in Table 3A but with NaCl concentrations of 0%, 1%, 5%, 10%, and 15%, and rheology in the form of shear viscosity between 0.2 rad/sec to 100 rad/sec was measured. The data in FIG. 5 indicate that salt concentrations even as high as 15% did not significantly affect the shear viscosity of aqueous compositions comprising the inventive emulsion stabilizers, relative to such compositions containing 0% NaCl. This absence of salt sensitivity allows greater flexibility in determining the ultimate composition of a composition such as a personal care formulation when using the emulsion stabilizer of the present invention, because there need not be concern that the presence of salts would disrupt the rheological behavior of the final product.

Example 6

Tactile Properties

The following examples in Table 5 show that when HM-EHEC 1 is blended with cross-linked, modified starch, Starch A, more desirable tactile properties are achieved than when HM-EHEC 1 is used alone.

Hydrophobically modified cellulose ethers generally have higher viscosity and elastic modulus than cross-linked, modified starches, and in theory could be used alone as emulsion stabilizers. In practice, however, hydrophobically modified cellulose ethers have undesirable tactile qualities when used in personal care formulations. It is a challenge to provide an emulsion stabilizer that includes enough of the hydrophobically modified cellulose ether to provide the desired emulsion stability, but not so much as to make the final product unacceptable to the consumer with respect to tactile qualities. Further, the cross-linked, modified starch must be present in an amount sufficient to not only overcome the undesirable tactile properties associated with the hydrophobically modified cellulose ether, but also to increase gel strength (G') to overcome creaming or syneresis (gravity effect).

Five formulations comprising varying amounts of hydrophobically modified cellulose ether and modified, cross-linked starch were prepared and evaluated for tactile properties. Each formulation also contained 0.25% Tween® 40 (a nonionic ethoxylated (20) sorbitan ester surfactant, available from Croda Inc., Edison, N.J.), 0.55% Span® 80 (a nonionic sorbitan oleate surfactant available from Croda Inc., Edison, N.J.). 30% triglyceride-based oil in the form of safflower oil, 0.5% Glydant preservative, and the balance water. The compositions are listed in Table 6. Based on the study, the biopolymer blends at 2% total polymer concentrations with 50% and about 75% of modified starch in total polymers generates desirable sense of touch.

TABLE 5

Formulations for tactile evaluation

|  | HM-EHEC 1 | Starch A |
|---|---|---|
| Formulation 15 (Comparative) | 12 0% | 2.0% |
| Formulation 16 | 0.5% | 1.5% |
| Formulation 17 | 1.00% | 1.00% |
| Formulation 18 (Comparative) | 1.5% | 0.5% |
| Formulation 19 (Comparative) | 2% | 0% |

Figure 6:
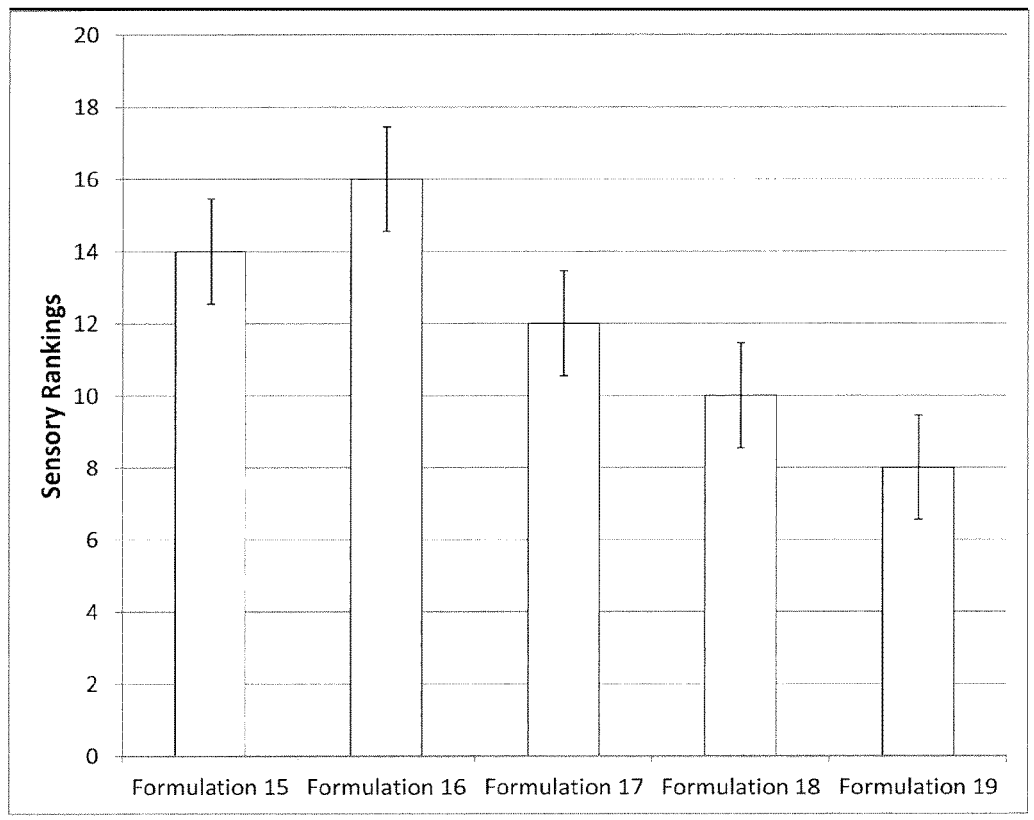
FIG. 6 is a graph illustrating the sensory rankings of compositions comprising biopolymer blends having different proportions of a hydrophobically modified cellulose ether and a cross-linked, modified starch, in accordance with Example 6.

Five panelists each were asked to rank two formulations following the scheme listed in Table 6. A 30 μL sample of each formulation was applied on each panelist's pre-washed inner forearm. Panelists rubbed the Formulations onto their skin for 20 seconds and chose which of the two samples was tactilely preferred. For example, if a panelist was given two formulations, X and Y, if the panelist preferred Y over X, then Formulation Y was given a score of 2 and Formulation X was given a score of 1. The overall rankings for each Formulation are the sums of each test by each panelist, listed as Rank Sum in Table 6 and illustrated in FIG. 6. A ranking difference greater than 2.9 was considered a statistically significant difference. A difference of 2.9 or less indicated that there was no statistical difference.

TABLE 6

Tactile test results of the five Formulations listed in Table 6

| Block | Panelist | Formulation 15 (comparative) | Formulation 16 | Formulation 17 | Formulation 18 | Formulation 19 (comparative) |
|---|---|---|---|---|---|---|
| 1 | 1 | 1 | 2 |  |  |  |
| 2 | 2 |  |  | 2 | 1 |  |
| 3 | 3 |  |  | 2 |  | 1 |
| 4 | 4 | 2 |  | 1 |  |  |
| 5 | 5 |  |  |  | 2 | 1 |
| 6 | 1 |  |  | 2 |  | 1 |

TABLE 6-continued

Tactile test results of the five Formulations listed in Table 6

| Block | Panelist | Formulation 15 (comparative) | Formulation 16 | Formulation 17 | Formulation 18 | Formulation 19 (comparative) |
|---|---|---|---|---|---|---|
| 7 | 2 | 2 | | | | 1 |
| 8 | 3 | 2 | | | 1 | |
| 9 | 4 | | 2 | | 1 | |
| 10 | 5 | | 2 | 1 | | |
| 11 | 1 | | | | 2 | 1 |
| 12 | 2 | 2 | | 1 | | |
| 13 | 3 | | | 2 | 1 | |
| 14 | 4 | 1 | 2 | | | |
| 15 | 5 | | 2 | | | 1 |
| 16 | 1 | | 2 | 1 | | |
| 17 | 2 | | 2 | | 1 | |
| 18 | 3 | 2 | | | | 1 |
| 19 | 4 | | | 2 | | 1 |
| 20 | 5 | 2 | | | | 1 |
| | Rank Sum: | 14 | 16 | 12 | 10 | 8 |

The results show that Formulation 16 ranked the highest with respect to tactile qualities. This result is surprising, because it would not have been expected that a formulation that included hydrophobically modified cellulose ether in addition to starch would have tactile qualities at least as good as if not better than a formulation of starch alone. It was not expected that replacing a portion of the starch with hydrophobically modified cellulose ether would lead to an improvement in tactile properties. Formulation 15 gave good tactile qualities but in the absence of any hydrophobically modified cellulose ether it would not be expected to function as an emulsion stabilizer to provide long term stability.

Example 7

Stability of Triglyceride-based Emulsion Containing Higher Level of Polymers with Lower Molecular Weight of Hydrophobic Modified EHEC Samples of the hydrophobically modified EHEC with lower molecular weight but at higher levels were blended with cross-linked, modified starch, also at higher levels, to make emulsion formulations, which is based on safflower oils, as shown in Table 7. Both Formulation 20 and Formulation 21 contained 0.25% Tween® 40 (a nonionic ethoxylated (20) sorbitan ester surfactant, available from Croda Inc., Edison, N.J.), 0.55% Span® 80 (a nonionic sorbitan oleate surfactant available from Croda Inc., Edison, N.J.), 30% triglyceride-based oil in the form of safflower oil, 0.5% Glydant® preservative , and the balance water. In each Formulation, 2.4% of an HM-EHEC (see Table 1) and 2.6% of Starch A are used. The data in Table 7 demonstrates that the blends of either of HM-EHEC with lower molecular weight compared to HM-EHEC 1 and the cross-linked, modified Starch A provided excellent emulsion stability for the triglyceride-based (i.e. safflower oil) emulsions when used at the appropriate load value in the emulsion composition.

TABLE 7

Stability of HM-EHEC/Starch Blend Stabilized Triglyceride Oil Emulsions.

| | Modified cellulosic used | HM-EHEC Usage Level | Starch A | Stability (d) |
|---|---|---|---|---|
| Formulation 20 | HM-EHEC 2 | 2.4% | 2.6% | >28 |
| Formulation 21 | HM-EHEC 3 | 2.4% | 2.6% | >28 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

We claim:

1. An emulsion stabilizer comprising:
   a blend of one or more cellulose ether and one or more cross-linked, modified starch, wherein one or more of the cellulose ethers is hydrophobically modified by substitution with one or more aliphatic or aromatic, saturated or unsaturated, linear, branched or cyclic hydrophobic groups comprising from 8 to 30 carbon atoms, and wherein the total amount of cellulose ethers in the blend is not greater than 50 wt %.

2. The emulsion stabilizer of claim 1 wherein said one or more of the cellulose ethers is a hydrophobically modified non-ionic cellulose ether.

3. The emulsion stabilizer of claim 2 wherein the non-ionic cellulose ether is selected from the group consisting of methyl cellulose, ethyl cellulose, propyl cellulose, butyl cellulose, hydroxyethyl cellulose, methylhydroxyethyl cellulose, ethylhydroxyethyl cellulose, methylethylhydroxyethyl cellulose, propylhydroxyethylcellulose, hydroxypropylmethyl cellulose, hydroxypropylethyl cellulose, hydroxypropylpropyl cellulose, hydroxypropyl hydroxyethyl cellulose, methyl hydroxypropyl hydroxyethyl cellulose, hydroxypropyl cellulose, and mixtures thereof.

4. The emulsion stabilizer of claim 1 wherein the one or more hydrophobically modified cellulose ether has a weight average molecular weight of 900,000 or greater.

5. The emulsion stabilizer of claim 1 wherein the one or more cellulose ether is derived from hardwood pulp, softwood pulp, cotton sources including cotton linters, bacterial cellulose or regenerated cellulose.

6. The emulsion stabilizer of claim 1 wherein the cross-linked, modified starch is hydrophilic.

7. The emulsion stabilizer of claim 1 wherein the cross-linked, modified starch is water soluble.

8. The emulsion stabilizer of claim 1 wherein the cross-linked, modified starch is derived from corn, wheat, rice, sorghum, pea, potato, tapioca (cassava), sweet potato, and sago.

9. The emulsion stabilizer of claim 1 wherein the cross-linked, modified starch has an amylopectin content of greater than 90 %.

10. A personal care formulation comprising an oil-in-water emulsion and the emulsion stabilizer of claim 1 wherein the emulsion stabilizer is present in an amount from about 1 wt % to about 6 wt % based on the total weight of the formulation.

11. The personal care formulation of claim 10 wherein the hydrophobically modified one or more cellulose ether has a weight average molecular weight of 900,000 or greater and the emulsion stabilizer is present at about 1 wt % to about 3 wt % based on the total weight of the formulation.

12. The personal care formulation of claim 10 wherein the hydrophobically modified one or more cellulose ether has a weight average molecular weight of less than 900,000 and the emulsion stabilizer is present at about 3 wt % to about 6 wt % based on the total weight of the formulation.

13. The personal care formulation of claim 10 wherein the personal care formulation is a hair styling composition.

14. The personal care formulation of claim 10 where the oil is selected from hydrocarbon-based oils and natural oils.

15. The personal care formulation of claim 10 wherein the oil is about 10-50% by weight of the emulsion.

* * * * *